US009675755B2

(12) United States Patent
Shick et al.

(10) Patent No.: US 9,675,755 B2
(45) Date of Patent: Jun. 13, 2017

(54) SYRINGE FILTER

(75) Inventors: Leemen Loy Shick, Duluth, GA (US); Brian W. King, Cheshire (GB)

(73) Assignee: National Scientific Company, Rockwood, TN (US)

( * ) Notice: Subject to any disclaimer, the term of this patent is extended or adjusted under 35 U.S.C. 154(b) by 0 days.

(21) Appl. No.: 13/438,939

(22) Filed: Apr. 4, 2012

(65) Prior Publication Data
US 2013/0264266 A1   Oct. 10, 2013

(51) Int. Cl.
B01D 35/00 (2006.01)
A61M 5/165 (2006.01)
A61M 5/36 (2006.01)
B01D 63/08 (2006.01)

(52) U.S. Cl.
CPC ............ A61M 5/165 (2013.01); A61M 5/36 (2013.01); B01D 63/087 (2013.01); A61M 2005/1657 (2013.01); B01D 2313/08 (2013.01); B01D 2325/08 (2013.01)

(58) Field of Classification Search
CPC ....... B01D 61/14; B01D 61/142; B01D 63/08
USPC .......................... 422/534, 535, 560, 565, 566
See application file for complete search history.

(56) References Cited

U.S. PATENT DOCUMENTS

| 3,932,153 A | 1/1976 | Byrns |
| 3,938,513 A | 2/1976 | Hargest |
| 4,056,100 A | 11/1977 | Noiles |
| 4,137,917 A | 2/1979 | Cohen |
| 4,159,954 A | 7/1979 | Gangemi |
| 4,404,006 A | 9/1983 | Williams et al. |
| 4,444,661 A * | 4/1984 | Jackson et al. ............... 210/446 |
| 5,076,933 A * | 12/1991 | Glenn et al. .................. 210/641 |
| 5,269,917 A | 12/1993 | Stankowski |
| 5,443,723 A | 8/1995 | Stankowski et al. |
| 5,792,354 A * | 8/1998 | Aksberg ....................... 210/406 |

(Continued)

FOREIGN PATENT DOCUMENTS

| DE | 2354269 A1 | 5/1975 |
| EP | 0 102 748 A2 | 3/1984 |
| GB | 2 318 525 | * 4/1998 ............. B01D 29/01 |

OTHER PUBLICATIONS

Dia-Nielsen GMBH & Co., Screen-captures of syringe filters acquired from http://www.dia-nielsen.de/, (2008) 46 pages.

(Continued)

Primary Examiner — Jill Warden
Assistant Examiner — Dwayne K Handy
(74) Attorney, Agent, or Firm — Wood Herron & Evans LLP

(57) ABSTRACT

A syringe filter for containing a filter membrane is disclosed and includes first and second fluid distribution surfaces configured to be positioned on opposing sides of a membrane. An inlet port is in fluid communication with the first fluid distribution surface and a first plurality of distribution pathways formed on the first fluid distribution surface. An outlet port is in fluid communication with the second fluid distribution surface and a second plurality of distribution pathways formed on the second fluid distribution surface. The first plurality of distribution pathways is configured to distribute fluid flow from the inlet port to one side of the membrane while the second plurality of distribution pathways is configured to direct fluid flow from another side of the membrane to the outlet port.

32 Claims, 11 Drawing Sheets

(56) References Cited

U.S. PATENT DOCUMENTS

2001/0000061 A1   3/2001  Myers
2003/0199847 A1*  10/2003 Akerlund et al. ............ 604/411
2011/0224648 A1   9/2011  Secci

OTHER PUBLICATIONS

SUN-SRI, Screen-captures of syringe filters acquired from http://www.sun-sri.com/products, (2009) 6 pages.
Espacenet, English Machine Translation of Publication No. FR2647512A1, published on Nov. 30, 1990, retrieved from http://worldwide.espacenet.com on Jun. 25, 2013 (5 pages).
European Patent Office, International Search Report and Written Opinion of the International Searching Authority, International Application No. PCT/US2013/035253, mailed on Jun. 18, 2013 (10 pages).
The International Bureau of WIPO, International Preliminary Report on Patentability, International Application No. PCT/US2013/035253, date of issuance Oct. 7, 2014 (7 pages).
Espacenet, English Machine Translation of Abstract for DE2354269A1, published on May 7, 1975, retrieved from http://worldwide.espacenet.com on May 25, 2016 (1 page).
Chinese Patent Office, Office Action, Chinese Application No. 201380027844.9, mailed Apr. 19, 2016 (13 pages).

* cited by examiner

SYRINGE FILTER

FIELD OF THE INVENTION

The present invention relates generally to filtration devices and, more particularly, to syringe filtration devices.

BACKGROUND

Syringe filters are single-use filter cartridges that are conventionally used to remove particulates from fluids used in sample preparation protocols, such as during HPLC analysis, ion chromatography, or dissolution testing. In other instances, syringe filters may be coupled to a syringe to remove particulates during a hypodermic injection.

While known conventional syringe filter design has provided a much needed benefit to such uses, there remains some need for improvement. This is particularly true for the manufacture process—high scrap rates, labor-intensive inspection processes, inconsistent product appearance, and periodic contamination of raw materials are just a few of the deficiencies in manufacturing that are experienced.

Furthermore, known conventional product designs include connection ports that are fragile and subject to breakage. Additionally, the syringe filter has a generally low burst pressure, leading to filter failure and possible reduction in the integrity of analysis results.

As a result, there exists a need for a syringe filter design that lends itself to a more cost efficient manufacture and that reduces the occurrence of blockage and/or filter failure.

SUMMARY OF THE INVENTION

The present invention overcomes the foregoing problems and other shortcomings, drawbacks, and challenges of known conventional syringe filter designs. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a syringe filter includes first and second fluid distribution surfaces configured to be positioned on opposing sides of a membrane. An inlet port is in fluid communication with the first fluid distribution surface and a first plurality of distribution pathways formed on the first fluid distribution surface. An outlet port is in fluid communication with the second fluid distribution surface and a second plurality of distribution pathways formed on the second fluid distribution surface. The first plurality of distribution pathways is configured to distribute fluid flow from the inlet port to one side of the membrane while the second plurality of distribution pathways is configured to direct fluid flow from another side of the membrane to the outlet port.

Another embodiment of the present invention is directed to a syringe filter for containing a filter membrane. The syringe filter includes an inlet portion and an outlet portion. The inlet portion includes a first fluid distribution surface having a first perimetric edge and an inlet port in fluid communication therewith. The outlet portion includes a second fluid distribution surface having a second perimetric edge and an outlet port in fluid communication therewith. First and second pluralities of distribution pathways are formed on the first and second fluid distribution surfaces, respectively. The first plurality of distribution pathways is configured to direct fluid flow from the inlet port toward the first perimetric edge while the second plurality of distribution pathways is configured to direct fluid flow from the second perimetric edge to the outlet port. Each of the first and second fluid distribution surfaces is configured to be positioned on opposing sides of a filter membrane.

Still another embodiment of the present invention is directed to a syringe filter comprising a filter membrane, an inlet portion, and an outlet portion. The filter membrane is configured to remove at least one particulate from a fluid moving through the syringe filter. The inlet portion includes a first fluid distribution surface positioned on one side of the filter membrane. The inlet portion further includes an inlet port in fluid communication with the first fluid distribution surface and a first plurality of distribution pathways formed on the first fluid distribution surface. The outlet portion includes a second fluid distribution surface positioned on another side of the filter membrane. The outlet portion further includes an outlet port in fluid communication with the second fluid distribution surface and a second plurality of distribution pathways formed on the second surface. The first plurality of distribution pathways is configured to distribute fluid flow from the inlet port across one side of the membrane while the second plurality of distribution pathways is configured to direct filtered fluid flow from another side of the membrane to the outlet port.

Still another embodiment of the present invention is directed to a syringe filter containing a filter membrane and including an inlet portion and an outlet portion. The inlet portion includes a first fluid distribution surface and an inlet port in fluid communication therewith. The outlet portion includes a second fluid distribution surface and an outlet port in fluid communication therewith. A ring is positioned on one of the first and second fluid distribution surfaces and has an angular profile across its radial dimension. The other of the first and second fluid distribution surfaces includes a toothed surface that is aligned with the ring. The toothed surface, when the first distribution surface is positioned adjacent the second fluid distribution surface, is configured to receive the ring. When the ring is compressed against the toothed surface, the compressed ring and toothed surface is configured to resist rotational movement of the first fluid distribution surface relative to the second fluid distribution surface.

The above and other objects and advantages of the present invention shall be made apparent from the accompanying drawings and the descriptions thereof.

BRIEF DESCRIPTION OF THE FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION

Figure 1:
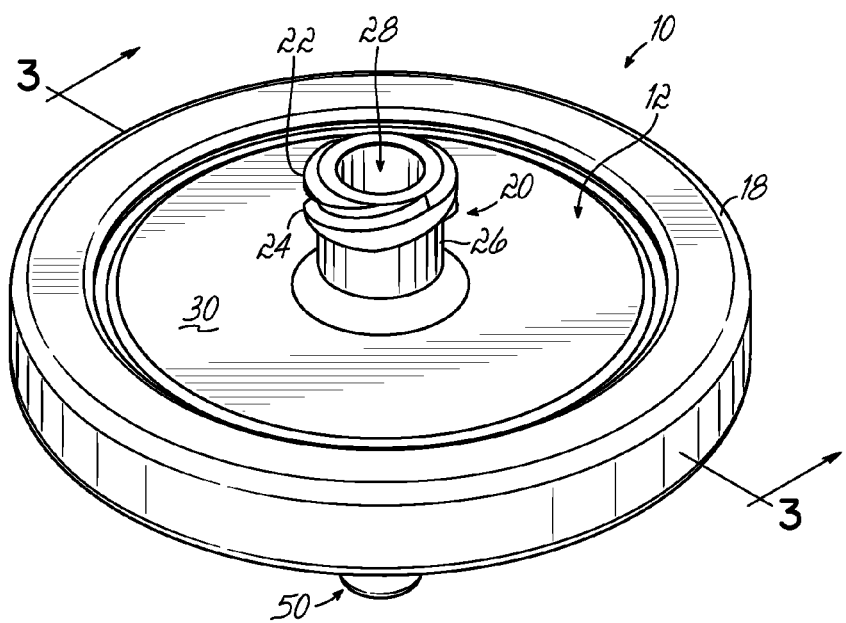
FIG. 1 is a perspective view of a syringe filter in accordance with one embodiment of the present invention.
Figure 2:
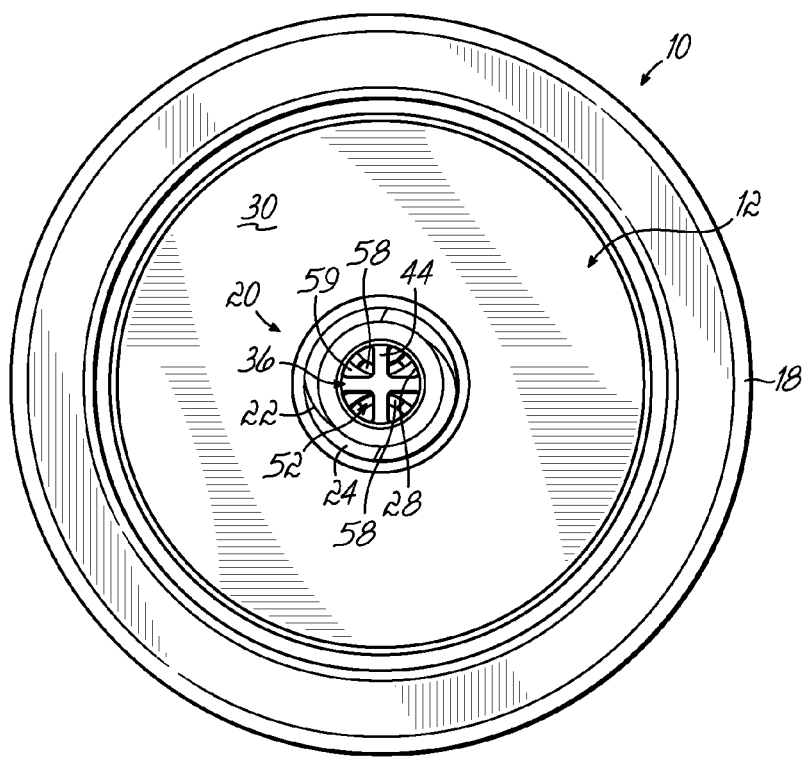
FIG. 2 is a top view of the syringe filter of FIG. 1.
Figure 3:
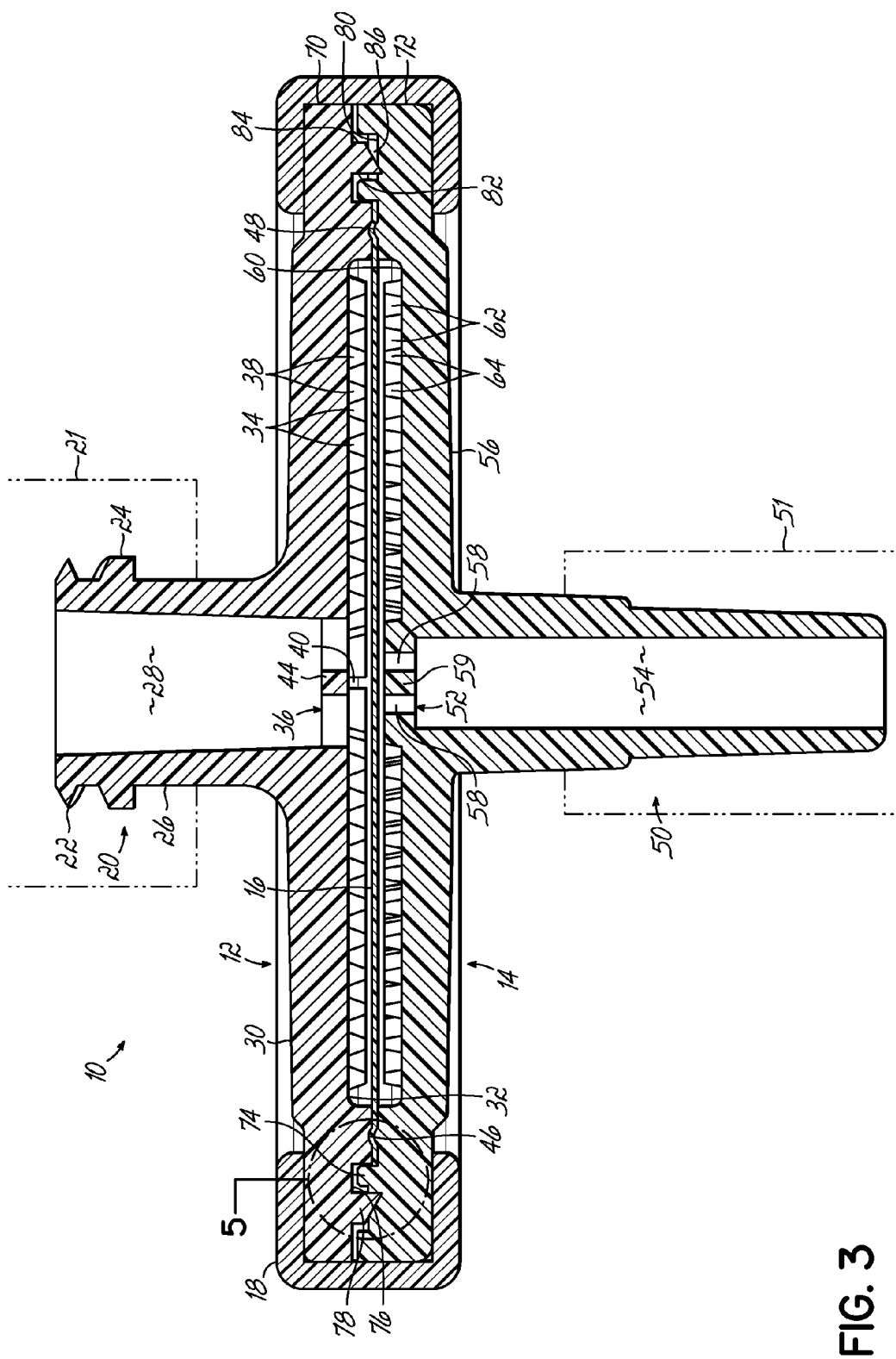
FIG. 3 is an assembled, cross-sectional view of the syringe filter of FIG. 1 and taken along the line 2-2.

Turning now to the figures, and in particular to FIGS. 1-3, a syringe filter 10 in accordance with one embodiment of the present invention is shown. While not required, the particular illustrative embodiment is shown as a 30 mm syringe filter (i.e., suitable for use with a 30 mm luer lock).

The syringe filter 10 includes an inlet portion 12, an outlet portion 14, a membrane 16 located therebetween, and a sealing ring 18 surrounding at least an edge of the inlet portion 12 and the outlet portion 14. The membrane 16 may be selected, at least in part, by the particular application and fluid filtration needs. For example, the membrane 16 may range in construction materials (for example, polytetrafluoroethylene, polysulfone, nylon, polyvinylidene fluoride, cellulose, cellulose acetate, polypropylene, glass microfiber, and so forth) and porosity (with pores ranging from about 0.2 µm to about 5 µm).

The inlet and outlet portions 12, 14 may be constructed from a moldable, chemically resistant, inert polymeric material, including, for example, polypropylene and polyethylene.

Referring specifically now to the inlet portion 12, the inlet portion 12 may include a luer lock 20 that is configured to form a fluid tight connection with a syringe 21, a tube, or other similar fluid supply device. The luer lock 20 may include one or more leads 22 to at least one thread 24 configured to threadably engage the syringe 21 when making the fluid tight connection.

A neck 26 extends from the luer lock 20 and includes a fluid lumen 28 therein, and an inlet base 30 extends, outwardly and radially, from the neck 26 to a size and shape that is suitable for receiving the membrane 16. A fluid distribution surface 32 of the inlet base 30 includes a plurality of distribution pathways 34 configured to direct a fluid that is entering the inlet portion 12 through the lumen 28 and generally uniformly across the membrane 16.

Figure 4:
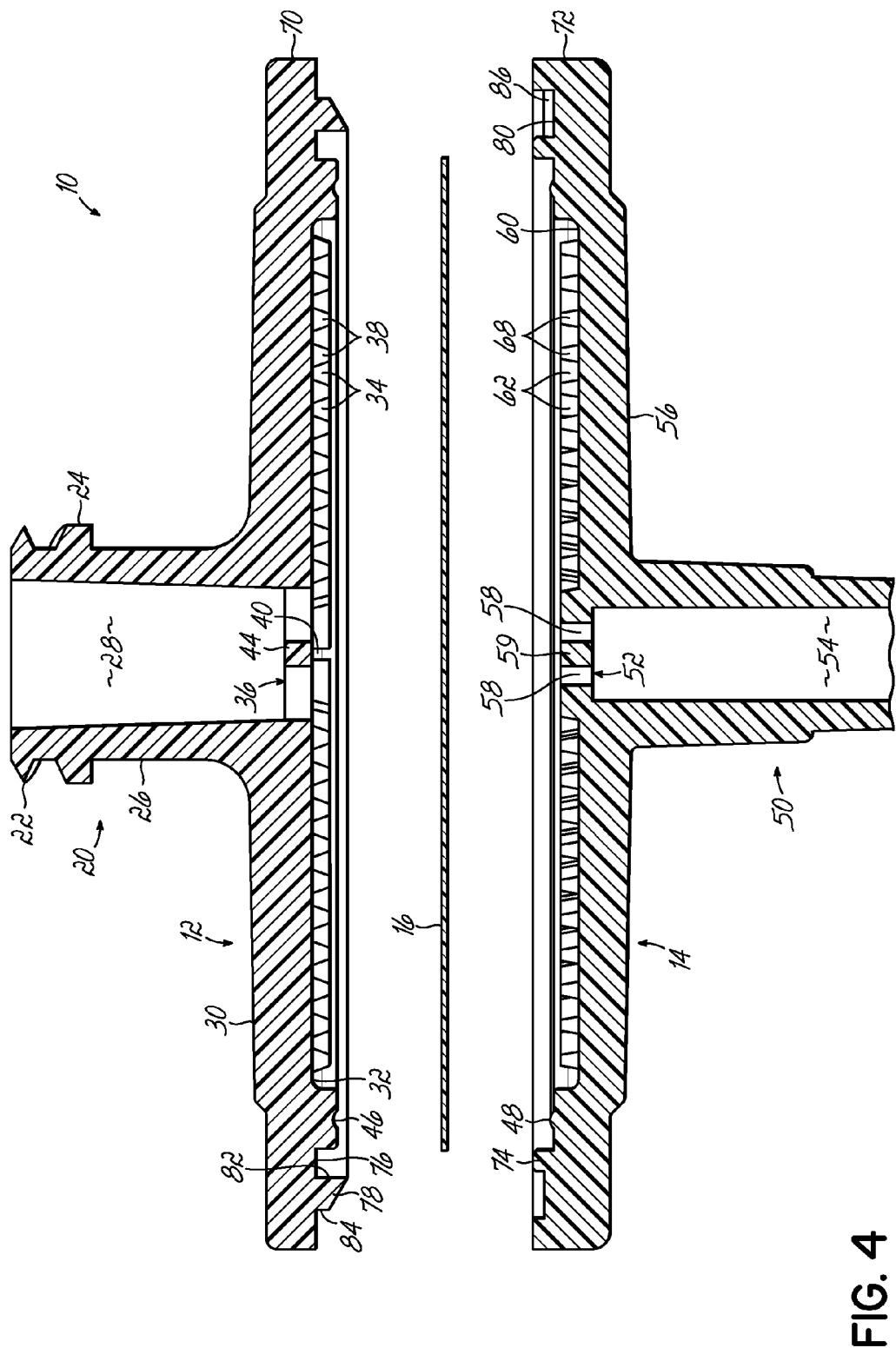
FIG. 4 is an exploded, cross-sectional view of the syringe filter of FIG. 1.

While the number, shape, and size of the plurality of distribution pathways 34 may vary, the distribution pathways 34, as shown in FIG. 4, surround a central inlet port 36 that is in fluid communication with the fluid lumen 28, and are defined a plurality of a concentric, discontinuous circles positioned radially outwardly therefrom. Still more specifically, the plurality of concentric circles is comprised of one or more concentric lugs 38, with one or more channels 40 located therebetween and extending radially outwardly from the central inlet port 36. Distribution pathways 34 are defined between each radially-successive pair of concentric lugs 38. By partitioning the fluid distribution surface 32 into the plurality of distribution pathways 34 and the plurality of channels 40, fluid flow rate is increased and the distribution of fluid over a surface of the membrane 16 more controlled.

While not specifically shown, it would be readily appreciated by those of ordinary skill in the art that the concentric circles may also comprise one or more outer, concentric circles, alone or in combination with the concentric lugs 38. Alternatively still, the fluid distribution pathways 34 may be ovoid, ellipsoidal, or other shape as necessary or desired for the particular syringe filter construction.

The lugs 38 may be formed with blunt or beveled edges and with the channels 40 being circumferentially spaced about the inlet base 30 in a radial pattern extending from the central inlet port 36; however, this is not necessary and the channels 40 may be offset in other patterns relative to each other if so desired. It would be readily understood that the number of lugs 38 need not be limited to the particular number or arrangement as shown herein. Furthermore, it would be readily understood that the distribution pathways 34 need not be uniform in radial width nor uniformly separated.

The lugs 38 may have various profiles. For example, the profile of the lugs 38 may be trapezoid, triangular, or square. The edges of the profile may be abrupt or rounded, depending on the desired degree of fluid turbulence. The profile also need not be uniform across all lugs 38 of the fluid distribution surface 32.

Figure 6:
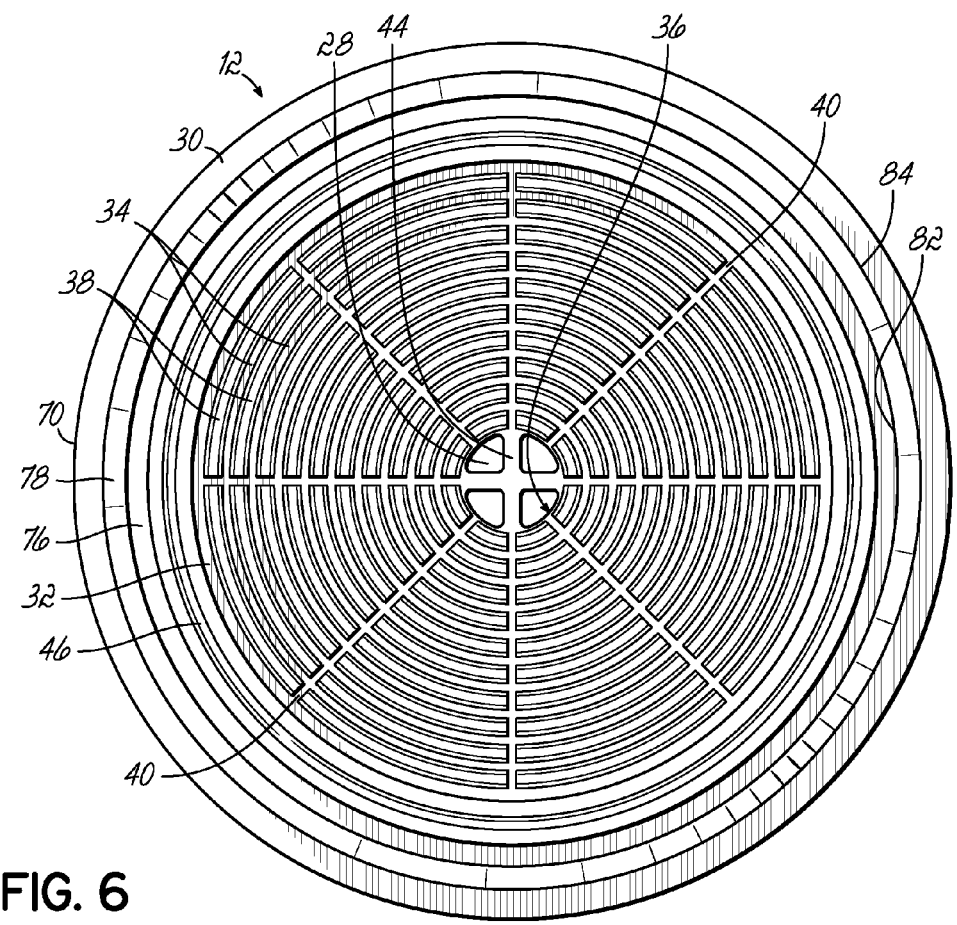
FIG. 6 is a bottom view of an inlet filter supporting surface of the syringe filter of FIG. 1.

The central inlet port 36 may be substantially circular in shape and may optionally include one or more ribs, of which two orthogonal, intersecting ribs 44 extending across the diameter of the central inlet port 28 are shown, to divide the central inlet port 28 into two or more sub-ports (shown herein as quadrants). While the intersecting ribs 44 are shown to be in alignment with four of the channels 40 in FIG. 6, this structure and design are not necessary.

Referring specifically now to FIGS. 3 and 4, a membrane securement groove 46 may be positioned radially outwardly from the distribution pathways 34 of the inlet portion 12 and, with a membrane securement ring 48 of the outlet portion 14, captures and secures the membrane 16 within the syringe filter 10 as described in greater detail below.

Figure 7:
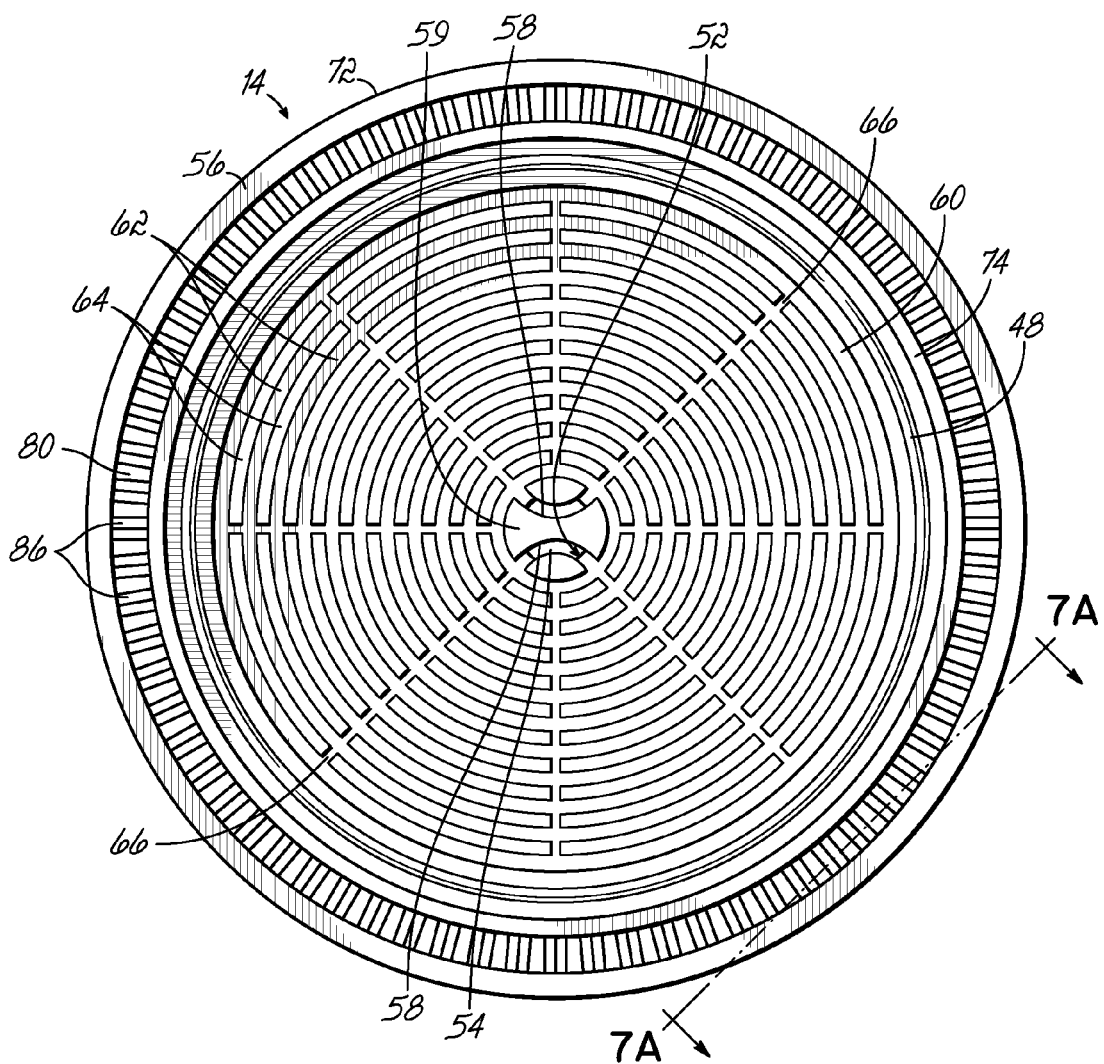
FIG. 7 is a top view of an outlet filter supporting surface of the syringe filter of FIG. 1.

With reference again to FIGS. 1-3 and now FIG. 7, the details of the outlet portion 14 are described in greater detail. The outlet portion 14 includes a luer taper 50 in fluid communication with a central outlet port 52. The luer taper 50 includes an outer shape, a lumen therethrough, and is configured to form a fluidic coupling with a tubing 51, a needle, or other fluid receiving device.

As was described above with reference to the inlet portion 12, the outlet portion 14 expands, outward radially, to an outlet base 56 having a size and shape that is suitable for receiving the membrane 16. An outer dimension of the outlet base 56 is substantially similar to an outer dimension of the inlet base 30 such that the two portions 12, 14 may be coupled together, as described below.

A fluid distribution surface 60 of the outlet base 56 includes a plurality of distribution pathways 62 therein. The distribution pathways 62 are configured to direct the fluid, filtered by the membrane 16, toward the central outlet port 52 and into the lumen 54 of the luer taper 50.

As was described above with respect to the inlet portion 12, the distribution pathways 62 of the outlet base 56 may also vary in number, shape, and size and surround the central outlet port 52. As shown, the plurality of concentric, discontinuous circles positioned radially outwardly from the central outlet port 52 includes concentric lugs 64 with one or more channels 66 located therebetween and extending radially outwardly therefrom. Still more specifically, the plurality of concentric circles is comprised of one or more concentric lugs 64, with one or more channels 66 located therebetween and extending radially outwardly from the central outlet port 52. Distribution pathways 62 are defined between each radially-successive pair of concentric lugs 64. In some embodiments, not necessary shown herein, concentric circles may be used in place or, or in addition to, the concentric lugs 64. In use with the outlet portion 14, the lugs 64 increase the number of fluid channels and improve the flow rate through the syringe filter.

The lugs 64 may be formed with a blunt or beveled edge with the channels 66 being circumferentially spaced about the outlet base 56 in a radial pattern extending from the central outlet port 52; however, this is not necessary and the channels 66 may be offset in other patterns relative to each other if so desired.

The central outlet port 52 of the outlet portion 14 may include one or more fluid communicating pathways 58 extending through a centrally-positioned membrane support 59. For example, and specifically shown in FIG. 7, two arc-shaped fluid communicating pathways 58 extend through the membrane support 59, each arc pathway 58 being aligned with two different ones of the channels 66. This arrangement of the arc pathways 58 facilitates flow from the distribution rings 62, along the channels 66, and into the pathways 58 leading to the central outlet port 52. Furthermore, the membrane support 59 resists blockage of the outlet port 52, which may occur in other known syringe filter designs by a fluid flow-induced vacuum drawing the membrane 16 (FIG. 3) into the central outlet port 52. While the particular illustrative embodiment of the membrane support 59 includes a large central portion and two smaller, diametrically opposing portions, it would be understood by those of ordinary skill in the art that this structure and arrangement is not required and that other arrangements and structures may also be used.

FIG. 2 is a top view of the vertically aligned inlet and outlet ports 36, 52. As shown, the intersecting ribs 44 of the central inlet port 36 are offset with respect to the fluid pathways 58 of the central outlet port 52. The alignment supports the membrane 16 via the membrane support 59 while maximizing fluid communication between the inlet and outlet portions 12, 14.

Figure 5:
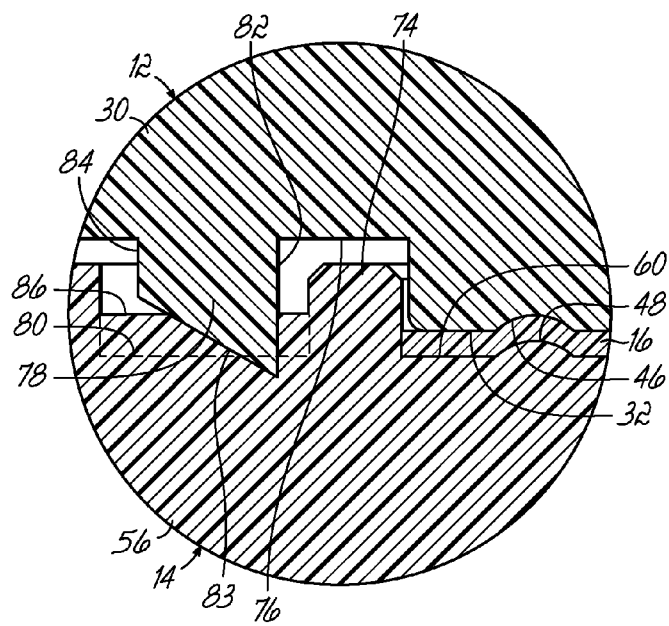
FIG. 5 is an enlarged view of the sealing features encircled 5 in FIG. 3.

Turning now to FIGS. 3-5, structures of the outer perimetric edges 70, 72 of the inlet and outlet portions 12, 14, respectively, are described in accordance with one embodiment of the present invention. A first ring 74 and a first groove 76 of the outlet and inlet portions 14, 12, respectively, are positioned at a first radial distance from the central inlet and outlet ports 36, 52. When positioned together, the first ring 74 and the first groove 76 are configured to aid in proper alignment of the inlet portion 12 with the outlet portion 14.

A second ring 78 depending from the fluid distribution surface 32 of the inlet base 30 is positioned at a second radial distance from the central inlet and outlet ports 36, 52, wherein the second radial distance is greater than the first radial distance. The second ring 78 may be continuous and circumferentially-positioned about the central inlet port 36 or, alternatively, the second ring 78 may be discontinuous and comprise of one or more lugs extending circumferentially about the central inlet port 36. In any event, the profile of the second ring 78, as shown in FIG. 5, may include a first upstanding wall 82 having a length, with respect to a top wall of the groove 76, that exceeds a length of an opposing second upstanding wall 84. An inclined wall 83 extends radially inwardly between the walls 82, 84 as shown in FIG. 5.

Figure 7A:
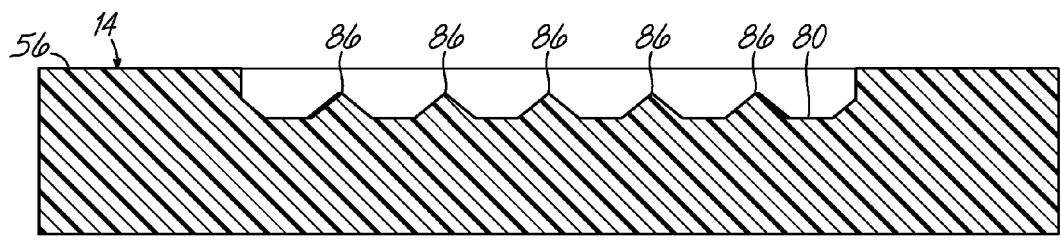
FIG. 7A is an enlarged view of a toothed surface encircled 7A in FIG. 7.

The second ring 78 is received by a toothed surface 80 on the fluid distribution surface 60 of the outlet base 56. As shown in FIGS. 7 and 7A, the toothed surface 80 includes a plurality of circumferentially-spaced teeth 86. Because the inlet and outlet portions 12, 14 are generally constructed of a polymeric material, as the second ring 78 is brought into contact with the toothed surface 80, the first wall 82 of the second ring 78 contacts the teeth 86 (FIG. 7) of the toothed surface 80. Further contact may cause at least one of the teeth 86 (FIG. 7) and the first wall 82 to compress, at least partially. This compression is configured to resist rotational movement of the inlet portion 12 with respect to the outlet portion 14 and forms a fluid-tight coupling between the same.

When coupled in this manner, the channels 40 of the inlet portion 12 may be vertically aligned with the channels 66 of the outlet portion 14 to facilitate efficient fluid communication between the central inlet and outlet ports 36, 52 and across the membrane 16. However, this arrangement should not be considered to be limiting.

With reference again to FIG. 3, after the inlet and outlet portions 12, 14 are assembled with the membrane 16 secured therebetween, a third fluid-tight seal may be formed by placing the sealing ring 18 circumferentially around, and extending over at least a portion of, outer perimetric edges 70, 72 of the inlet and outlet portions 12, 14. While not required, the sealing ring 18 may be secured to the inlet and outlet portions 12, 14, for example, by an appropriate adhesive or ultrasonic welding. In some embodiments, the sealing ring 18 may include a color or indicia that is indicative of the membrane 18 contained therein.

With reference now to FIGS. 8-14, a syringe filter 100 is described in accordance with yet another embodiment of the present invention. The syringe filter 100 is similar to the syringe filter 10 of FIG. 1; however, the syringe filter 100 is sized and shaped for use as 17 mm syringe filter (i.e., suitable for use with a 17 mm luer lock).

The syringe filter 100 includes an inlet portion 102, an outlet portion 104, a membrane 106 therebetween, and a sealing ring 108 surrounding at least an edge of the inlet portion 102 and the outlet portion 104. The membrane 106, as was discussed above, may be selected, at least in part, by the particular application and fluid filtration needs.

The inlet and outlet portions 102, 104 may be constructed from a moldable, chemically resistant, inert polymeric material, including, for example, polypropylene and polyethylene. Still other materials may include polycarbonate, polymethylpentene, acrylic or acrylic blends, polyterephthlate ("PET"), glycol-modified PET copolyester ("PETG"), cyclic olefin copolymers, polysulfone, and/or acrylonitrile butadiene styrene.

The inlet portion 102 may include a luer lock 110 configured to form a fluid tight connection with a syringe 111 or other fluid supply device (as was described above). The luer lock 110 may include one or more leads 112 to at least one thread 114 configured to threadably engage the syringe 111.

A neck 116 extends from the luer lock 110 and includes a fluid lumen 118 therein, and an inlet base 120 extends, outwardly and radially, from the neck 116 to a size and shape that is suitable for receiving the membrane 106. A fluid distribution surface 122 of the inlet base 120 includes a plurality of distribution pathways 124 configured to direct a fluid that is entering the inlet portion 102 through the lumen 118 and uniformly across the membrane 106.

As discussed above, the number, shape, and size of the plurality of distribution pathways 124 may vary, and may be different from the distribution pathways 34 (FIG. 3) of the syringe filter 10 (FIG. 1) described previously. The number, shape, and size of the distribution pathways 34 (FIG. 3) being determined, at least in part, by the size of the particular fluid supply device (e.g., the syringe 111). For instance, the 30 mm syringe filter 10 of FIG. 1, having a larger diameter as compared to the 17 mm syringe filter 100, may be operably to filter a larger volume of fluid received from a larger volume syringe as compared with a smaller diameter filter. Yet, one of ordinary skill in the art would readily appreciate the interplay between the number, shape, and size of the distribution pathways 124, as well as the porosity of the membrane 106, determine the volume and pressure capacities of a particular syringe filter.

The distribution pathways 124 are defined by a plurality of discontinuous, concentric circles positioned radially outwardly from a central inlet port 126. Still more specifically, the plurality of concentric circles is comprised of one or more concentric lugs 128, with one or more channels 130 located therebetween and extending radially outwardly from the central inlet port 126. Distribution pathways 124 are defined between each radially-successive pair of concentric lugs 128. Again, by partitioning the fluid distribution surface 122 into the plurality of distribution pathways 124 and the plurality of channels 130, fluid flow rate is increased.

While not specifically shown, it would be readily appreciated by those of ordinary skill in the art that the concentric circles may also comprise one or more outer, concentric circles, alone or in combination with the concentric lugs 128. Alternatively still, the fluid distribution pathways 124 may be ovoid, ellipsoidal, or other shape as necessary or desired for the particular syringe filter construction.

The lugs 128 may be formed with blunt or beveled edges and with the channels 130 being circumferentially spaced about the inlet base 120 in a radial pattern extending from the central inlet port 126; however, this is not necessary and the channels 130 may be offset in other patterns relative to each other if so desired. It would be readily understood that the number of lugs 128 need not be limited to the particular number or arrangement as shown herein. Furthermore, it would be readily understood that the distribution pathways 124 need not be uniform in radial width nor uniformly separated.

The lugs 128 may have various profiles. For example, the profile of the lugs 128 may be trapezoid, triangular, or square. The edges of the profile may be abrupt or rounded, depending on the desired degree of fluid turbulence. The profile also need not be uniform across all lugs 128 of the fluid distribution surface 122.

The central inlet port 126 may be substantially circular in shape and may optionally include one or more ribs, of which two orthogonal, intersecting ribs 134 are shown, to divide the central inlet port 126 into two or more sub-ports (shown herein as quadrants). While the intersecting ribs 134 are shown to be in alignment with four of the channels 130 in FIG. 12, this structure and design are not necessary.

Figure 10:
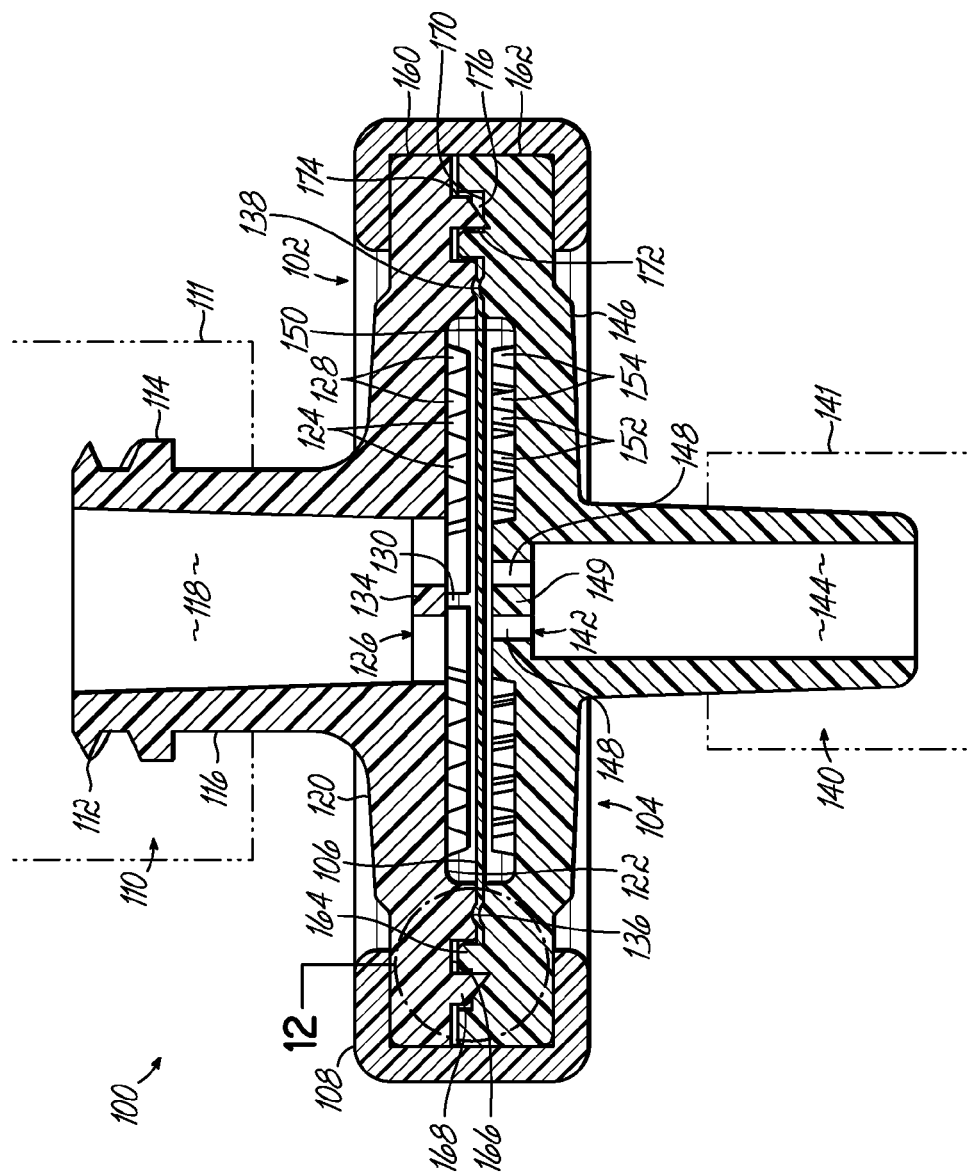
FIG. 10 is an assembled, cross-sectional view of the syringe filter of FIG. 8 and taken along the line 10-10.
Figure 11:
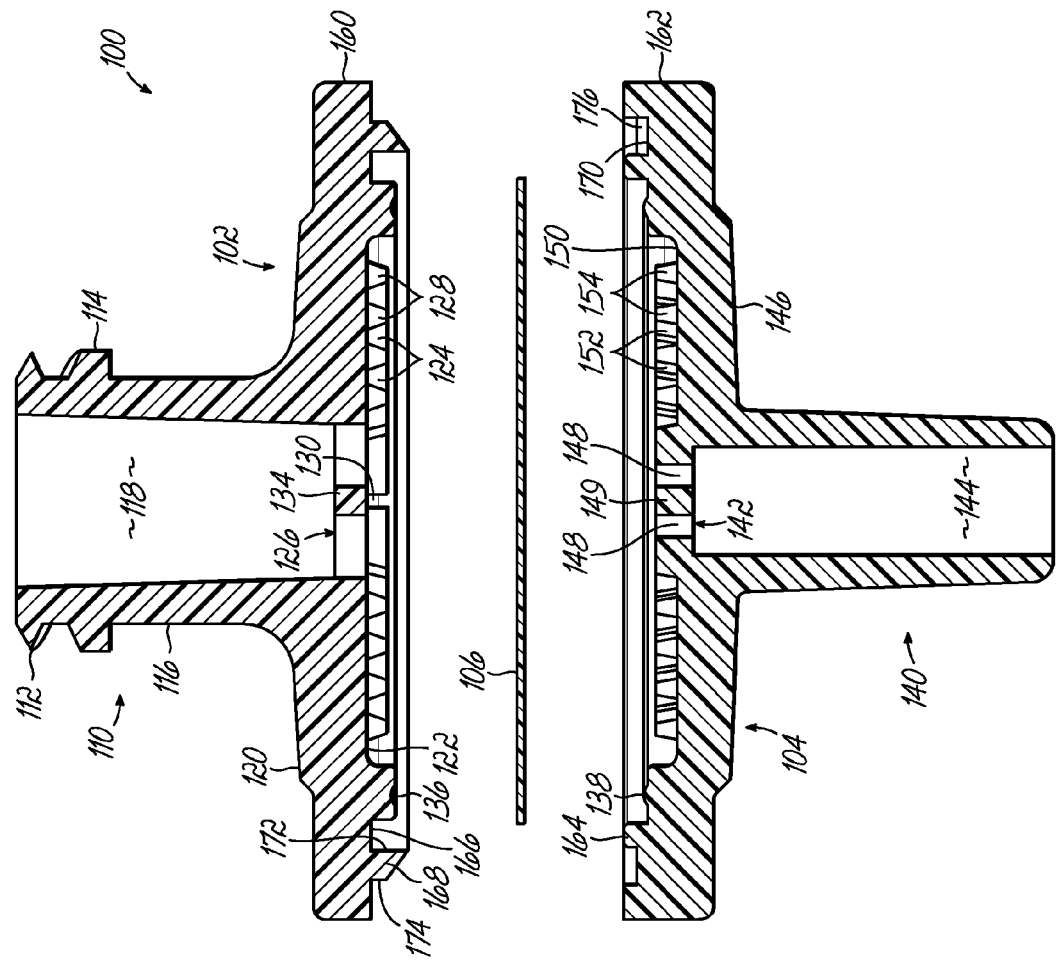
FIG. 11 is an exploded, cross-sectional view of the syringe filter of FIG. 8.
Figure 12:
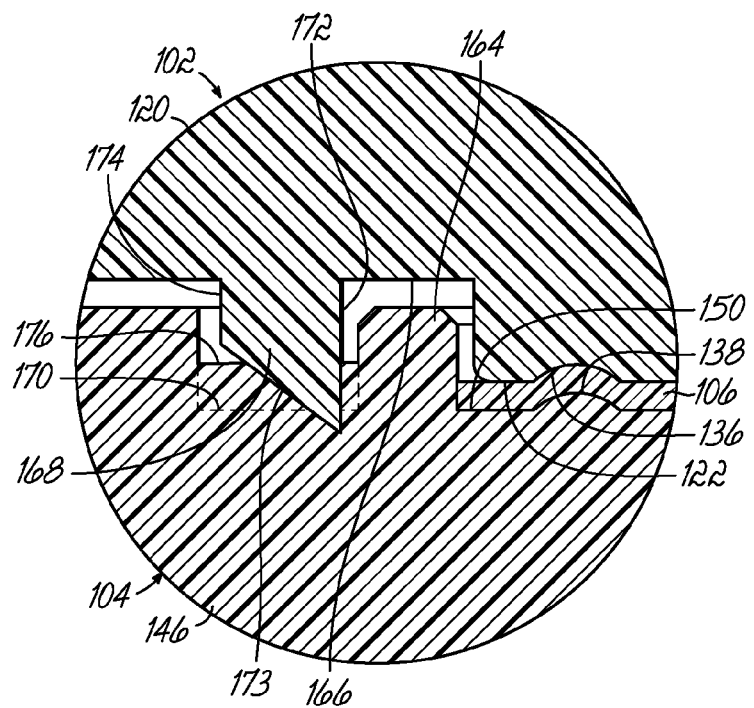
FIG. 12 is an enlarged view of a sealing feature encircled 12 in FIG. 10.
Figure 13:
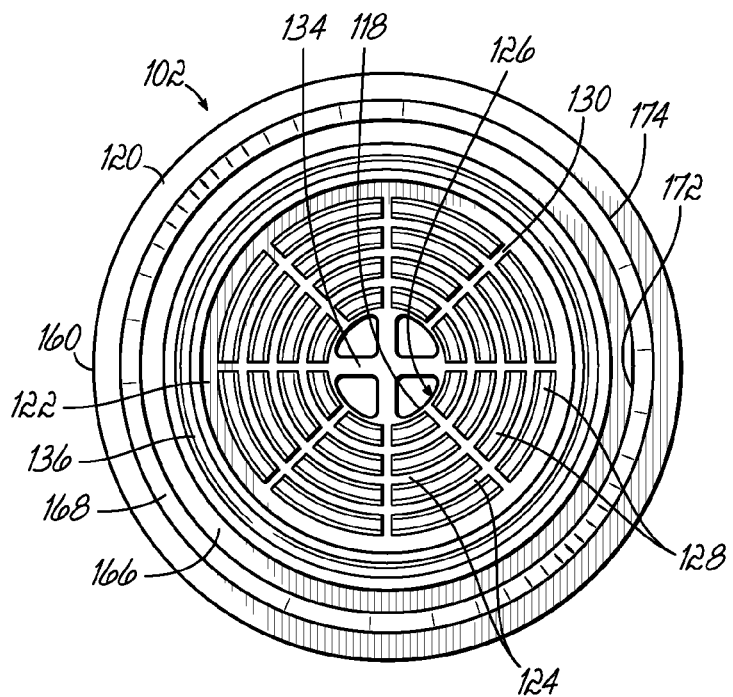
FIG. 13 is a bottom view of an inlet filter supporting surface of the syringe filter of FIG. 8.

Referring specifically to FIGS. 10-12, a membrane securement groove 136 may be positioned radially outward from the distribution pathways 124 of the inlet portion 102 and, with a membrane securement ring 138 of the outlet portion 104, captures and secures the membrane 106 within the syringe filter 100 as described in detail above.

With reference again to FIGS. 8-10 and now 14, the details of the outlet portion 104 are described in greater detail. The outlet portion 104 includes a luer taper 140 in fluid communication with a central outlet port 142. The luer taper 140 includes an outer shape, a lumen 144 therethrough, and is configured to form a fluidic coupling with a tubing 141 or other fluid receiving device.

As was described above with reference to the inlet portion 102, the outlet portion 104 expands, outward radially, to an outlet base 146 having a size and shape that is suitable for receiving the membrane 106. An outer dimension of the outlet base 146 is substantially similar to an outer dimension of the inlet base 120 such that the two portions 102, 104 may be coupled together, as described below.

A fluid distribution surface 150 of the outlet base 146 includes a plurality of distribution pathways 152 therein. The distribution pathways 152 are configured to direct the fluid, filtered by the membrane 16, toward the central outlet port 142 and into the lumen 144 of the luer taper 140.

The distribution pathways 152 of the outlet base 146 may also vary in number, shape, and size and surround the central outlet port 142. As shown, the plurality of concentric, discontinuous circles positioned radially outwardly from the central outlet port 142 includes concentric lugs 154 with one or more channels 156 located therebetween and extending radially outwardly therefrom. Still more specifically, the plurality of concentric circles is comprised of one or more concentric lugs 154, with one or more channels 156 located therebetween and extending radially outwardly from the central outlet port 142. Distribution pathways 152 are defined between each radially-successive pair of concentric lugs 154. In some embodiments, not necessary shown herein, concentric circles may be used in place or, or in addition to, the concentric lugs 154. In use with the outlet portion 104, the lugs 154 increase the number of fluid channels 156 and improve the flow rate through the syringe filter 100.

Again, the concentric lugs 154 may be formed with a blunt or beveled edge with the channels 156 being circumferentially spaced about the outlet base 146 in a radial pattern extending from the central outlet port 142; however, this is not necessary and the channels 156 may be offset in other patterns relative to each other if so desired.

Figure 14A:
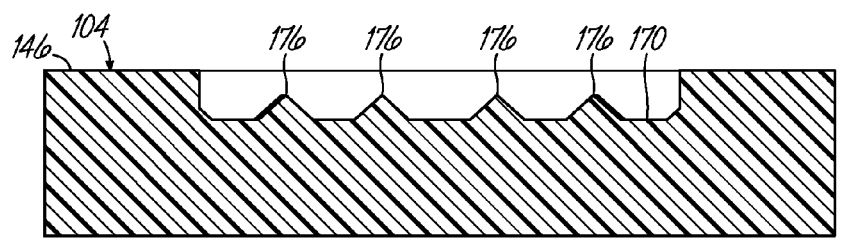
FIG. 14A is an enlarged view of a toothed surface encircled 14A in FIG. 14.
Figure 8:
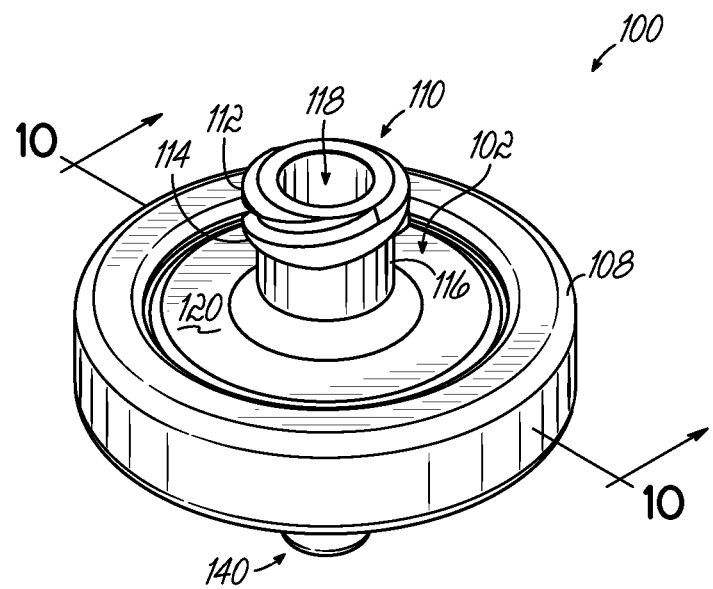
FIG. 8 is a perspective view of a syringe filter in accordance with another embodiment of the present invention.
Figure 14:
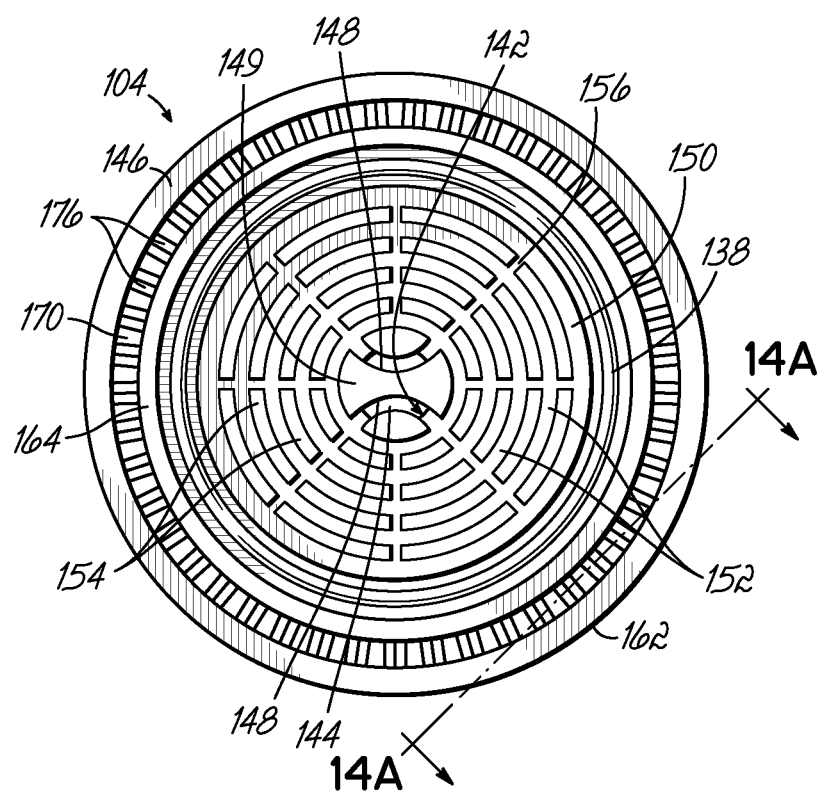
FIG. 14 is a top view of an outlet filter supporting surface of the syringe filter of FIG. 8.

In FIG. 14, the central outlet port 142 of the outlet portion 104 is shown and includes one or more fluid communicating pathways 148 extending through a centrally-positioned membrane support 149. For example, two arc-shaped fluid communicating pathways 148 extend through the membrane support 149, each art pathway 148 being aligned with two different ones of the channels 156. This arrangement of the arc pathways 148 facilitates flow from the distribution rings 152, along the channels 156, and into the pathways 148 leading to the central outlet port 142. Furthermore, the membrane support 149 resists blockage of the outlet port 142, which may occur in other known syringe filter designs by a fluid flow-induced vacuum drawing the membrane 156 (FIG. 10) into the central outlet port 142. While the particular illustrative embodiment of the membrane support 149 includes a large central portion and two smaller, diametrically opposing portions, it would be understood by those of ordinary skill in the art that this structure and arrangement is not required and that other arrangements and structures may also be used.

Figure 9:
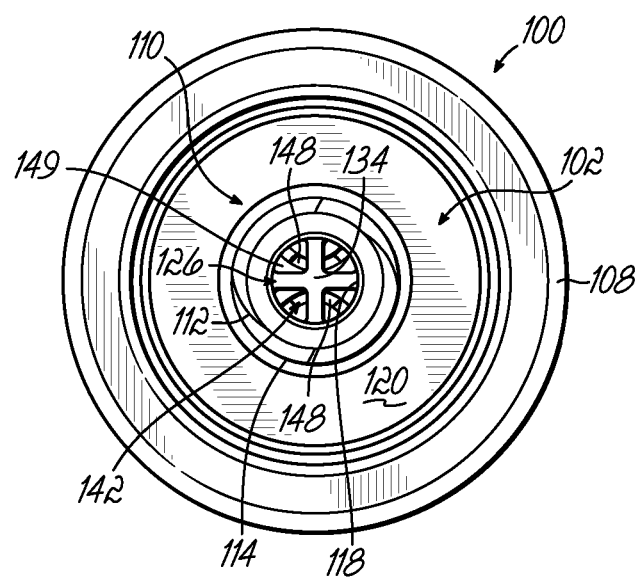
FIG. 9 is a top view of the syringe filter of FIG. 8.

FIG. 9 is a top view of the vertically aligned inlet and outlet ports 128, 142. As shown, the intersecting ribs 134 of the central inlet port 126 are offset with respect to the fluid pathways 148 of the central outlet port 142. This alignment supports the membrane 156 via the membrane support 149 while maximizing fluid communication between the inlet and outlet portions 102, 104.

Turning now to FIGS. 10-12, structures of the outer perimetric edges 160, 162 of the inlet and outlet portions 102, 104, respectively, are described in accordance with one embodiment of the present invention. A first ring 164 and a first groove 166 of the outlet and inlet portions 104, 102, respectively, are positioned at a first radial distance from the inlet and outlet ports 136, 142. When positioned together, the first ring 164 and the first groove 166 are configured to aid in proper alignment of the inlet portion 102 with the outlet portion 104.

A second ring 168 depending from the fluid distribution surface 122 of the inlet base 120 is positioned at a second radial distance from the central inlet and outlet ports 126, 142, wherein the second radial distance is greater than the first radial distance. The second ring 168 may be continuous and circumferentially-positioned about the central inlet port 126 or, alternatively, the second ring 168 may be discontinuous and comprise of one or more lugs extending circumferentially about the central inlet port 126. In any event, the second ring 168 may include a first upstanding wall 172 having a length, with respect to a top wall of the groove 166, that exceeds a length of an opposing second upstanding wall 174. An inclined wall 173 extends radially inwardly between the walls 172, 174, as shown in FIG. 12.

The second ring 168 is received by a toothed surface 170 on the fluid distribution surface 150 of the outlet base 146. As shown in FIGS. 14 and 14B, the toothed surface 170 includes a plurality of circumferentially-spaced teeth 176. Because the inlet and outlet portions 102, 104 are generally constructed of a polymeric material, as the second ring 168 is brought into contact with the toothed surface 170, the first wall 172 of the second ring 168 contacts the teeth 176 (FIG. 14) of the toothed surface 170. Further contact may cause at least one of the teeth 176 (FIG. 14) and the first wall 172 to compress, at least partially. This compression is configured to resist rotational movement of the inlet portion 102 with respect to the outlet portion 104 and forms a fluid-tight coupling between the same.

When coupled in this manner, the channels 130 of the inlet portion 102 may be vertically aligned with the channels 156 of the outlet portion 104 to facilitate efficient fluid communication between the central inlet and outlet ports 126, 142 and across the membrane 106. However, this arrangement should not be considered to be limiting.

With reference again to FIG. 10, after the inlet and outlet portions 102, 104 are assembled with the membrane 106 secured therebetween, a third fluid-tight seal may be formed by placing the sealing ring 108 circumferentially around, and extending over at least a portion of, the outer perimetric edges 160, 162 of the inlet and outlet portions 102, 104. While not required, the sealing ring 108 may be secured to the inlet and outlet portions 102, 104, for example, by an appropriate adhesive or ultrasonic welding. In some embodiments, the sealing ring 108 may include a color or indicia that is indicative of the membrane 108 contained therein.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicants' invention.

What is claimed is:

1. A syringe filter for containing a filter membrane, comprising:
    a first fluid distribution surface configured to be positioned on one side of the filter membrane;
    an inlet port in fluid communication with the first fluid distribution surface;
    a first plurality of distribution pathways formed on the first fluid distribution surface and in fluid communication with the inlet port;
    at least one first fluid channel formed on the first distribution surface and in fluid communication with the first plurality of distribution pathways;
    a second fluid distribution surface generally opposing the first fluid distribution surface and configured to be positioned on another side of the filter membrane;
    an outlet port in fluid communication with the second fluid distribution surface;
    a second plurality of distribution pathways formed on the second fluid distribution surface and in fluid communication with the outlet port;
    at least one second fluid channel formed on the second distribution surface and in fluid communication with the second plurality of distribution pathways;
    a membrane positioned between and supported by the first and second fluid distribution surfaces, the membrane being configured to remove at least one particulate from a fluid moving from the first fluid distribution surface, across the membrane, to the second fluid distribution surface;
    a membrane retention ring on at least one of the first and second fluid distribution surfaces, the membrane retention ring configured to engage the membrane when the membrane is positioned between the first and second fluid distribution surfaces and to form a fluid tight seal between the membrane and the first and second fluid distribution surfaces; and
    a membrane retention groove on the other of the first and second fluid distribution surfaces and aligned with the membrane retention ring, the membrane retention groove configured to receive the membrane retention ring when the membrane retention ring forms the fluid tight seal between the membrane and the first and second fluid distribution surfaces,
    wherein the first plurality of distribution pathways and the at least one first fluid channel are configured to distribute fluid flow from the inlet port to one side of the membrane and the second plurality of distribution pathways and the at least one second fluid channel are configured to direct fluid flow from another side of the membrane to the outlet port,
    and further wherein the outlet port includes a centrally-positioned membrane support and at least one fluid communicating pathway extending through the centrally-positioned membrane support.

2. The syringe filter of claim 1, further comprising:
    a first ring on at least one of the first and second fluid distribution surfaces and positioned radially outwardly from a membrane perimeter when the membrane is positioned adjacent the at least one of the first and second fluid distribution surfaces; and
    a first groove on the other of the first and second fluid distribution surfaces and aligned with the first ring, wherein the first groove is configured to receive the first ring when the first fluid distribution surface is positioned adjacent the second fluid distribution surface and to align the first fluid distribution surface with the second fluid distribution surface.

3. The syringe filter of claim 1, further comprising:
a second ring on at least one of the first and second fluid distribution surfaces and positioned radially outwardly from a membrane perimeter when the membrane is positioned adjacent the at least one of the first and second fluid distribution surfaces, the second ring having an angular profile across a radial dimension thereof; and
a toothed surface on the other of the first and second fluid distribution surfaces and aligned with the second ring,
wherein the toothed surface is configured to receive the second ring when the first fluid distribution support surface is positioned adjacent the second fluid distribution surface and, with compression, the second ring compressed against the toothed surface is configured to resist rotational movement of the first fluid distribution support surface relative to the second fluid distribution surface.

4. The syringe filter of claim 1, wherein the first plurality of distribution pathways comprises a plurality of concentric rings positioned radially outwardly from the inlet port.

5. The syringe filter of claim 4, wherein each of the plurality of concentric rings comprises of one or more lugs, the one or more lugs defining the at least one first fluid channel between successive ones of the one or more lugs, the at least one first fluid channel extending radially outwardly from the inlet port.

6. The syringe filter of claim 1, wherein the second plurality of distribution pathways comprises a plurality of concentric rings positioned radially outwardly from the inlet port.

7. The syringe filter of claim 6, wherein each of the plurality of concentric rings comprises of one or more lugs, the one or more lugs defining the at least one second fluid channel between successive ones of the one or more lugs, the at least one second fluid channel extending radially outwardly from the outlet port.

8. The syringe filter of claim 1, further comprising:
an inlet portion supporting the first fluid distribution surface and the inlet port; and
an outlet portion supporting the second fluid distribution surface and the outlet port.

9. The syringe filter of claim 8, wherein the inlet portion is configured to be secured to the outlet portion, with the membrane positioned therebetween, by adhesive or ultrasonic welding.

10. The syringe filter of claim 9, further comprising:
a sealing ring configured to surround the secured inlet and outlet portions and to form a fluid-tight seal therewith.

11. The syringe filter of claim 1, wherein the centrally-positioned membrane support is configured to extend across the outlet port and the at least one fluid communicating pathway fluidically couples the second fluid distribution surface with the outlet port through the centrally-positioned membrane support.

12. The syringe filter of claim 1, further comprising:
a luer lock having a lumen extending therethrough, the lumen being in fluid communication with the inlet port and configured to fluidically couple the inlet port to a fluid source.

13. A syringe filter for containing a filter membrane, comprising:

an inlet portion having a first fluid distribution surface having a first perimetric edge and an inlet port in fluid communication with the first fluid distribution surface;
a first plurality of distribution pathways formed in the first fluid distribution surface, the first plurality of distribution pathways configured to direct fluid flow from the inlet port toward the first perimetric edge of the first fluid distribution surface;
at least one first fluid channel formed on the first fluid surface and in fluid communication with the first plurality of distribution pathways;
an outlet portion having a second fluid distribution surface having a second perimetric edge and an outlet port in fluid communication with the second fluid distribution surface;
a second plurality of distribution pathways formed in the second fluid distribution surface, the second plurality of distribution pathways configured to direct fluid flow from the second perimetric edge of the second fluid distribution surface to the outlet port;
at least one second fluid channel formed on the second fluid surface and in fluid communication with the second plurality of distribution pathways;
a membrane positioned between and supported by the first and second fluid distribution surfaces, the membrane being configured to remove at least one particulate from a fluid moving from the first fluid distribution surface, across the membrane, to the second fluid distribution surface;
a membrane retention ring on at least one of the first and second fluid distribution surfaces, the membrane retention ring configured to engage the membrane when the membrane is positioned between the first and second fluid distribution surfaces and to form a fluid tight seal between the membrane and the first and second fluid distribution surfaces; and
a membrane retention groove on the other of the first and second fluid distribution surfaces and aligned with the membrane retention ring, the membrane retention groove configured to receive the membrane retention ring when the membrane retention ring forms the fluid tight seal between the membrane and the first and second fluid distribution surfaces,
wherein the first and second fluid distribution surfaces are configured to be positioned adjacent opposing sides of a filter membrane;
and further wherein the outlet port includes a centrally-positioned membrane support and at least one fluid communicating pathway extending through the centrally-positioned membrane support.

14. The syringe filter of claim 13, further comprising:
a first ring on at least one of the first and second fluid distribution surfaces and positioned radially outwardly from a membrane perimeter when the membrane is positioned adjacent the at least one of the first and second fluid distribution surfaces; and
a first groove on the other of the first and second fluid distribution surfaces and aligned with the first ring,
wherein the first groove is configured to receive the first ring when the first fluid distribution surface is positioned adjacent the second fluid distribution surface and to align the first fluid distribution surface with the second fluid distribution surface.

15. The syringe filter of claim 13, further comprising:
a second ring on at least one of the first and second fluid distribution surfaces and positioned radially outwardly from a membrane perimeter when the membrane is positioned adjacent the at least one of the first and second fluid distribution surfaces, the second ring having an angular profile across a radial dimension thereof; and a toothed surface on the other of the first and second fluid distribution surfaces and aligned with the second ring, wherein the toothed surface is configured to receive the second ring when the first fluid distribution support surface is positioned adjacent the second fluid distribution surface and, with compression, the second ring compressed against the toothed surface is configured to resist rotational movement of the first fluid distribution support surface relative to the second fluid distribution surface.

16. The syringe filter of claim 13, wherein the first plurality of distribution pathways comprises a plurality of concentric rings positioned radially outwardly from the inlet port.

17. The syringe filter of claim 16, wherein each of the plurality of concentric rings comprises of one or more lugs, the one or more lugs defining the at least one first fluid channel between successive ones of the one or more lugs, the at least one first fluid channel extending radially outwardly from the inlet port.

18. The syringe filter of claim 13, wherein the second plurality of distribution pathways comprises a plurality of concentric rings positioned radially outwardly from the inlet port.

19. The syringe filter of claim 18, wherein each of the plurality of concentric rings comprises of one or more lugs, the one or more lugs defining the at least one second fluid channel between successive ones of the one or more lugs, the at least one second fluid channel extending radially outwardly from the outlet port.

20. The syringe filter of claim 13, wherein the inlet portion is configured to be secured to the outlet portion, with the membrane positioned therebetween, by adhesive or ultrasonic welding.

21. The syringe filter of claim 20, further comprising:
a sealing ring configured to surround the secured inlet and outlet portions and to form a fluid-tight seal therewith.

22. The syringe filter of claim 13, wherein a centrally-positioned membrane support is configured to extend across the outlet port and the at least one fluid communicating pathway fluidically couples the second fluid distribution surface with the outlet port through the centrally-positioned membrane support.

23. A syringe filter comprising:
an inlet portion comprising:
a first fluid distribution surface positioned on one side of the filter membrane;
an inlet port in fluid communication first fluid distribution surface; and
a first plurality of distribution pathways formed on the first fluid distribution surface and in fluid communication with the inlet port;
at least one first fluid channel formed on the first fluid distribution surface and in fluid communication with the first plurality of distribution pathways;
an outlet portion comprising:
a second fluid distribution surface positioned on another side of the filter membrane;
an outlet port in fluid communication second fluid distribution surface;
a second plurality of distribution pathways formed on the second fluid distribution surface and in fluid communication with the outlet port; and at least one second fluid channel formed on the second fluid distribution surface and in fluid communication with the second plurality of distribution pathways;
a membrane positioned between and supported by the first and second fluid distribution surfaces, the membrane being configured to remove at least one particulate from a fluid moving from the first fluid distribution surface, across the membrane, to the second fluid distribution surface;
a membrane retention ring on at least one of the first and second fluid distribution surfaces, the membrane retention ring configured to engage the membrane when the membrane is positioned between the first and second fluid distribution surfaces and to form a fluid tight seal between the membrane and the first and second fluid distribution surfaces; and
a membrane retention groove on the other of the first and second fluid distribution surfaces and aligned with the membrane retention ring, the membrane retention groove configured to receive the membrane retention ring when the membrane retention ring forms the fluid tight seal between the membrane and the first and second fluid distribution surfaces,
wherein the first plurality of distribution pathways and the at least one first fluid channel are configured to distribute fluid flow from the inlet port across one side of the membrane and the second plurality of distribution pathways and the at least one second fluid channel are configured to direct filtered fluid flow from another side of the membrane to the outlet port,
and further wherein the outlet port includes a centrally-positioned membrane support and at least one fluid communicating pathway extending through the centrally-positioned membrane support.

24. The syringe filter of claim 23, further comprising:
a first ring on at least one of the first and second fluid distribution surfaces and positioned radially outwardly from a membrane perimeter when the membrane is positioned adjacent the at least one of the first and second fluid distribution surfaces; and
a first groove on the other of the first and second fluid distribution surfaces and aligned with the first ring,
wherein the first groove is configured to receive the first ring when the first fluid distribution surface is positioned adjacent the second fluid distribution surface and to align the first fluid distribution surface with the second fluid distribution surface.

25. The syringe filter of claim 23, further comprising:
a second ring on at least one of the first and second fluid distribution surfaces and positioned radially outwardly from a membrane perimeter when the membrane is positioned adjacent the at least one of the first and second fluid distribution surfaces, the second ring having an angular profile across a radial dimension thereof; and
a toothed surface on the other of the first and second fluid distribution surfaces and aligned with the second ring,
wherein the toothed surface is configured to receive the second ring when the first fluid distribution surface is positioned adjacent the second fluid distribution surface and, with compression, the second ring compressed against the toothed surface is configured to resist rotational movement of the first fluid distribution surface relative to the second fluid distribution surface.

26. The syringe filter of claim 23, wherein the centrally-positioned membrane support is configured to extend across the outlet port and the at least one fluid communicating pathway fluidically couples the second fluid distribution surface with the outlet port through the centrally-positioned membrane support.

27. A syringe filter for containing a filter membrane, comprising:
    a first fluid distribution surface configured to be positioned on one side of the filter membrane;
    an inlet port in fluid communication with the first fluid distribution surface;
    a first plurality of distribution pathways formed on the first fluid distribution surface and in fluid communication with the inlet port;
    at least one first fluid channel formed on said first fluid distribution surface and in fluid communication with the first plurality of distribution pathways;
    a second fluid distribution surface generally opposing the first fluid distribution surface and configured to be positioned on another side of the filter membrane;
    an outlet port in fluid communication with the second fluid distribution surface;
    a second plurality of distribution pathways formed on the second fluid distribution surface and in fluid communication with the outlet port;
    at least one second fluid channel formed on said second fluid distribution surface and in fluid communication with the second plurality of distribution pathways;
    a membrane positioned between and supported by the first and second fluid distribution surfaces, the membrane being configured to remove at least one particulate from a fluid moving from the first fluid distribution surface, across the membrane, to the second fluid distribution surface;
    a ring on at least one of the first and second fluid distribution surfaces and positioned radially outwardly from a membrane perimeter when the membrane is positioned adjacent the at least one of the first and second fluid distribution surfaces; and
    a groove on the other of the first and second fluid distribution surfaces and aligned with the ring,
    wherein the groove is configured to receive the ring when the first fluid distribution surface is positioned adjacent the second fluid distribution surface and to align the first fluid distribution surface with the second fluid distribution surface,
    wherein the first plurality of distribution pathways and the at least one first fluid channel are configured to distribute fluid flow from the inlet port to one side of the membrane and the second plurality of distribution pathways and the at least one second fluid channel are configured to direct fluid flow from another side of the membrane to the outlet port,
    and further wherein the outlet port includes a centrally-positioned membrane support and at least one fluid communicating pathway extending through the centrally-positioned membrane support.

28. A syringe filter for containing a filter membrane, comprising:
    a first fluid distribution surface configured to be positioned on one side of the filter membrane;
    an inlet port in fluid communication with the first fluid distribution surface;
    a first plurality of distribution pathways formed on the first fluid distribution surface and in fluid communication with the inlet port;
    at least one first fluid channel formed on the first fluid distribution surface and in fluid communication with the first plurality of distribution pathways;
    a second fluid distribution surface generally opposing the first fluid distribution surface and configured to be positioned on another side of the filter membrane;
    an outlet port in fluid communication with the second fluid distribution surface;
    a second plurality of distribution pathways formed on the second fluid distribution surface and in fluid communication with the outlet port;
    at least one second fluid channel formed on the second fluid distribution surface and in fluid communication with the second plurality of distribution pathways;
    a membrane positioned between and supported by the first and second fluid distribution surfaces, the membrane being configured to remove at least one particulate from a fluid moving from the first fluid distribution surface, across the membrane, to the second fluid distribution surface;
    a ring on at least one of the first and second fluid distribution surfaces and positioned radially outwardly from a membrane perimeter when the membrane is positioned adjacent the at least one of the first and second fluid distribution surfaces, the ring having an angular profile across a radial dimension thereof; and
    a toothed surface on the other of the first and second fluid distribution surfaces and aligned with the ring,
    wherein the toothed surface is configured to receive the ring when the first fluid distribution support surface is positioned adjacent the second fluid distribution surface and, with compression, the ring compressed against the toothed surface is configured to resist rotational movement of the first fluid distribution support surface relative to the second fluid distribution surface,
    wherein the first plurality of distribution pathways and the at least one first fluid channel are configured to distribute fluid flow from the inlet port to one side of the membrane and the second plurality of distribution pathways and the at least one second fluid channel are configured to direct fluid flow from another side of the membrane to the outlet port.

29. A syringe filter for containing a filter membrane, comprising:
    an inlet portion having a first fluid distribution surface having a first perimetric edge and an inlet port in fluid communication with the first fluid distribution surface;
    a first plurality of distribution pathways formed on the first fluid distribution surface, the first plurality of distribution pathways configured to direct fluid flow from the inlet port toward the first perimetric edge of the first fluid distribution surface;
    at least one first fluid channel formed on the first distribution surface and in fluid communication with the first plurality of distribution pathways;
    an outlet portion having a second fluid distribution surface having a second perimetric edge and an outlet port in fluid communication with the second fluid distribution surface;
    a second plurality of distribution pathways formed on the second fluid distribution surface, the second plurality of distribution pathways configured to direct fluid flow from the second perimetric edge of the second fluid distribution surface to the outlet port;
    at least one second fluid channel formed on the second fluid distribution surface and in fluid communication with the second plurality of distribution pathways;
    a membrane positioned between and supported by the first and second fluid distribution surfaces, the membrane being configured to remove at least one particulate from a fluid moving from the first fluid distribution surface, across the membrane, to the second fluid distribution surface;
a ring on at least one of the first and second fluid distribution surfaces and positioned radially outwardly from a membrane perimeter when the membrane is positioned adjacent the at least one of the first and second fluid distribution surfaces; and
a groove on the other of the first and second fluid distribution surfaces and aligned with the ring,
wherein the groove is configured to receive the ring when the first fluid distribution surface is positioned adjacent the second fluid distribution surface and to align the first fluid distribution surface with the second fluid distribution surface,
wherein the first and second fluid distribution surfaces is configured to be positioned adjacent opposing sides of a filter membrane;
and further wherein the outlet port includes a centrally-positioned membrane support and at least one fluid communicating pathway extending through the centrally-positioned membrane support.

30. A syringe filter for containing a filter membrane, comprising:
an inlet portion having a first fluid distribution surface having a first perimetric edge and an inlet port in fluid communication with the first fluid distribution surface;
a first plurality of distribution pathways formed on the first fluid distribution surface, the first plurality of distribution pathways configured to direct fluid flow from the inlet port toward the first perimetric edge of the first fluid distribution surface;
at least one first fluid channel formed on the first fluid distribution surface and in fluid communication with the first plurality of distribution pathways;
an outlet portion having a second fluid distribution surface having a second perimetric edge and an outlet port in fluid communication with the second fluid distribution surface;
a second plurality of distribution pathways formed on the second fluid distribution surface, the second plurality of distribution pathways configured to direct fluid flow from the second perimetric edge of the second fluid distribution surface to the outlet port;
at least one second fluid channel formed on the second fluid distribution surface and in fluid communication with the second plurality of distribution pathways;
a membrane positioned between and supported by the first and second fluid distribution surfaces, the membrane being configured to remove at least one particulate from a fluid moving from the first fluid distribution surface, across the membrane, to the second fluid distribution surface;
a ring on at least one of the first and second fluid distribution surfaces and positioned radially outwardly from a membrane perimeter when the membrane is positioned adjacent the at least one of the first and second fluid distribution surfaces, the ring having an angular profile across a radial dimension thereof; and
a toothed surface on the other of the first and second fluid distribution surfaces and aligned with the ring,
wherein the toothed surface is configured to receive the ring when the first fluid distribution support surface is positioned adjacent the second fluid distribution surface and, with compression, the ring compressed against the toothed surface is configured to resist rotational movement of the first fluid distribution support surface relative to the second fluid distribution surface,
wherein the first and second fluid distribution surfaces is configured to be positioned adjacent opposing sides of a filter membrane.

31. A syringe filter comprising:
a filter membrane configured remove at least one particulate from a fluid moving through the syringe filter;
an inlet portion comprising:
a first fluid distribution surface positioned on one side of the filter membrane;
an inlet port in fluid communication first fluid distribution surface; and
a first plurality of distribution pathways formed on the first fluid distribution surface and in fluid communication with the inlet port;
at least one first fluid channel formed on the first fluid distribution surface and in fluid communication with the first plurality of distribution pathways;
an outlet portion comprising;
a second fluid distribution surface positioned on another side of the filter membrane;
an outlet port in fluid communication second fluid distribution surface;
a second plurality of distribution pathways formed on the second fluid distribution surface and in fluid communication with the outlet port; and
at least one second fluid channel formed on the second fluid distribution surface and in fluid communication with the second plurality of distribution pathways;
a ring on at least one of the first and second fluid distribution surfaces and positioned radially outwardly from a membrane perimeter when the membrane is positioned adjacent the at least one of the first and second fluid distribution surfaces; and
a groove on the other of the first and second fluid distribution surfaces and aligned with the ring,
wherein the groove is configured to receive the ring when the first fluid distribution surface is positioned adjacent the second fluid distribution surface and to align the first fluid distribution surface with the second fluid distribution surface,
wherein the first plurality of distribution pathways and the at least one first fluid channel are configured to distribute fluid flow from the inlet port across one side of the membrane and the second plurality of distribution pathways and the at least one second fluid channel are configured to direct filtered fluid flow from another side of the membrane to the outlet port.

32. A syringe filter comprising:
a filter membrane configured remove at least one particulate from a fluid moving through the syringe filter;
an inlet portion comprising:
a first fluid distribution surface positioned on one side of the filter membrane;
an inlet port in fluid communication first fluid distribution surface; and
a first plurality of distribution pathways formed on the first fluid distribution surface and in fluid communication with the inlet port;
at least one first fluid channel formed on the first distribution surface and in fluid communication with the first plurality of distribution pathways;
an outlet portion comprising;
a second fluid distribution surface positioned on another side of the filter membrane;

an outlet port in fluid communication second fluid distribution surface;
a second plurality of distribution pathways formed on the second fluid distribution surface and in fluid communication with the outlet port; and
at least one second fluid channel formed on the second fluid distribution surface and in fluid communication with the second plurality of distribution pathways;
a ring on at least one of the first and second fluid distribution surfaces and positioned radially outwardly from a membrane perimeter when the membrane is positioned adjacent the at least one of the first and second fluid distribution surfaces, the ring having an angular profile across a radial dimension thereof; and
a toothed surface on the other of the first and second fluid distribution surfaces and aligned with the ring,
wherein the toothed surface is configured to receive the ring when the first fluid distribution surface is positioned adjacent the second fluid distribution surface and, with compression, the ring compressed against the toothed surface is configured to resist rotational movement of the first fluid distribution surface relative to the second fluid distribution surface,
wherein the first plurality of distribution pathways and the at least one first fluid channel are configured to distribute fluid flow from the inlet port across one side of the membrane and the second plurality of distribution pathways and the at least one second fluid channel are configured to direct filtered fluid flow from another side of the membrane to the outlet port,
and further wherein the outlet port includes a centrally-positioned membrane support and at least one fluid communicating pathway extending through the centrally-positioned membrane support.

* * * * *

UNITED STATES PATENT AND TRADEMARK OFFICE
CERTIFICATE OF CORRECTION

Page 1 of 3

PATENT NO. : 9,675,755 B2
APPLICATION NO. : 13/438939
DATED : June 13, 2017
INVENTOR(S) : Leemen Loy Shick It is certified that error appears in the above-identified patent and that said Letters Patent is hereby corrected as shown below:

In the Specification

In Column 2, Line 41, change "the compressed ring and toothed surface is configured" to --the compressed ring and toothed surface are configured--.

In Column 3, Line 62, change "are defined a plurality of a concentric," to --are defined as a plurality of concentric,--.

In Column 5, Line 9, change "not necessary shown herein," to --not necessarily shown herein,--.

In Column 5, Line 64, change "and comprise of one or more lugs" to --and comprise one or more lugs--.

In Column 7, Line 12, change "may be operably to filter a larger volume of fluid" to --may be operable to filter a larger volume of fluid--.

In Column 8, Line 32, change "not necessary shown herein," to --not necessarily shown herein,--.

In Column 8, Line 49, change "each art pathway 148 being aligned with two" to --each arc pathway 148 being aligned with two--.

In Column 9, Line 21, change "and comprise of one or more lugs" to --and comprise one or more lugs--.

In Column 9, Line 62, change "is not the intention of applicant" to --is not the intention of Applicants--.

Signed and Sealed this
Tenth Day of October, 2017

Joseph Matal
*Performing the Functions and Duties of the
Under Secretary of Commerce for Intellectual Property and
Director of the United States Patent and Trademark Office*

CERTIFICATE OF CORRECTION (continued)

U.S. Pat. No. 9,675,755 B2

In the Claims

In Claim 5, Column 11, Line 26, change "plurality of concentric rings comprises of one or more lugs," to --plurality of concentric rings comprises one or more lugs,--.

In Claim 7, Column 11, Line 36, change "plurality of concentric rings comprises of one or more lugs," to --plurality of concentric rings comprises one or more lugs,--.

In Claim 17, Column 13, Line 20, change "plurality of concentric rings comprises of one or more lugs," to --plurality of concentric rings comprises one or more lugs,--.

In Claim 19, Column 13, Line 30, change "plurality of concentric rings comprises of one or more lugs," to --plurality of concentric rings comprises one or more lugs,--.

In Claim 23, Column 13, Line 52, change "an inlet port in fluid communication first fluid distribution" to --an inlet port in fluid communication with the first fluid distribution--.

In Claim 23, Column 13, Line 63, change "an outlet port in fluid communication second fluid distribution" to --an outlet port in fluid communication with the second fluid distribution--.

In Claim 29, Column 17, Line 16, change "wherein the first and second fluid distribution surfaces is configured" to --wherein the first and second fluid distribution surfaces are configured--.

In Claim 30, Column 18, Line 3, change "wherein the first and second fluid distribution surfaces is configured" to --wherein the first and second fluid distribution surfaces are configured--.

In Claim 31, Column 18, Line 7, change "a filter membrane configured remove" to --a filter membrane configured to remove--.

In Claim 31, Column 18, Line 12, change "an inlet port in fluid communication first fluid distribution" to --an inlet port in fluid communication with the first fluid distribution--.

In Claim 31, Column 18, Line 20, change "an outlet portion comprising;" to --an outlet portion comprising:--.

In Claim 31, Column 18, Line 23, change "an outlet port in fluid communication second fluid distribution" to --an outlet port in fluid communication with the second fluid distribution--.

In Claim 32, Column 18, Line 52, change "a filter membrane configured remove" to --a filter membrane configured to remove--.

In Claim 32, Column 18, Line 57, change "an inlet port in fluid communication first fluid distribution" to --an inlet port in fluid communication with the first fluid distribution--.

In Claim 32, Column 18, Line 65, change "an outlet portion comprising;" to --an outlet portion

CERTIFICATE OF CORRECTION (continued)
U.S. Pat. No. 9,675,755 B2 comprising:--.

In Claim 32, Column 19, Line 1, change "an outlet port in fluid communication second fluid distribution" to --an outlet port in fluid communication with the second fluid distribution--.